(12) United States Patent
Zang

(10) Patent No.: US 12,252,538 B2
(45) Date of Patent: Mar. 18, 2025

(54) MONOCLONAL ANTIBODIES AGAINST IgV DOMAIN OF B7-H3 AND USES THEREOF

(71) Applicant: Albert Einstein College of Medicine, Bronx, NY (US)

(72) Inventor: Xingxing Zang, New York, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 873 days.

(21) Appl. No.: 17/294,560

(22) PCT Filed: Nov. 15, 2019

(86) PCT No.: PCT/US2019/061887
§ 371 (c)(1),
(2) Date: May 17, 2021

(87) PCT Pub. No.: WO2020/102779
PCT Pub. Date: May 22, 2020

(65) Prior Publication Data
US 2022/0010018 A1    Jan. 13, 2022

Related U.S. Application Data

(60) Provisional application No. 62/768,128, filed on Nov. 16, 2018.

(51) Int. Cl.
C07K 16/28    (2006.01)

(52) U.S. Cl.
CPC ...... *C07K 16/2827* (2013.01); *C07K 16/2809* (2013.01); *C07K 2317/24* (2013.01); *C07K 2317/31* (2013.01); *C07K 2317/76* (2013.01); *C07K 2317/92* (2013.01)

(58) Field of Classification Search
CPC .................................................. C07K 16/2827
USPC ..................................................... 424/139.1
See application file for complete search history.

(56) References Cited

U.S. PATENT DOCUMENTS

| | | | |
|---|---|---|---|
| 4,816,567 A | 3/1989 | Cabilly et al. | |
| 5,283,173 A | 2/1994 | Fields et al. | |
| 5,468,614 A | 11/1995 | Fields et al. | |
| 5,530,101 A | 6/1996 | Queen et al. | |
| 5,585,089 A | 12/1996 | Queen et al. | |
| 5,693,761 A | 12/1997 | Queen et al. | |
| 5,693,762 A | 12/1997 | Queen et al. | |
| 5,807,715 A | 9/1998 | Morrison et al. | |
| 5,866,692 A | 2/1999 | Shitara et al. | |
| 5,997,867 A | 12/1999 | Waldmann et al. | |
| 6,054,297 A | 4/2000 | Carter et al. | |
| 6,180,370 B1 | 1/2001 | Queen et al. | |
| 6,180,377 B1 | 1/2001 | Morgan et al. | |
| 6,210,671 B1 | 4/2001 | Co | |
| 6,331,415 B1 | 12/2001 | Cabilly et al. | |
| 6,350,861 B1 | 2/2002 | Co et al. | |
| 6,410,319 B1 | 6/2002 | Raubitshek et al. | |
| 6,982,321 B2 | 1/2006 | Winter | |
| 7,087,409 B2 | 8/2006 | Barbas, III et al. | |
| 7,446,191 B2 | 11/2008 | Jensen | |
| 7,514,537 B2 | 4/2009 | Jensen | |
| 8,822,647 B2 | 9/2014 | Jensen | |
| 2004/0087025 A1 | 5/2004 | June et al. | |
| 2009/0092612 A1* | 4/2009 | Takayama ................. | A61P 7/02 435/69.6 |
| 2011/0189141 A1 | 8/2011 | Kieback et al. | |
| 2011/0243972 A1 | 10/2011 | Jaffee | |
| 2017/0369585 A1 | 12/2017 | Orentas et al. | |
| 2018/0009899 A1 | 1/2018 | Griffin et al. | |

FOREIGN PATENT DOCUMENTS

| | | |
|---|---|---|
| EP | 0519596 A1 | 12/1992 |
| JP | 2017524725 A | 8/2017 |
| WO | 99/58572 A1 | 11/1999 |
| WO | 01/27160 A1 | 4/2001 |
| WO | 2003/046204 A2 | 6/2003 |
| WO | 2006016276 A2 | 2/2006 |
| WO | 2010065818 A1 | 6/2010 |
| WO | 2010/1133893 A1 | 11/2010 |
| WO | 2011109400 A2 | 9/2011 |
| WO | 2012147713 A1 | 11/2012 |
| WO | 2014031687 A1 | 2/2014 |
| WO | 2015/032906 A2 | 3/2015 |
| WO | 2015142675 A2 | 9/2015 |
| WO | 2015181267 A1 | 12/2015 |
| WO | 2017044699 A1 | 3/2017 |
| WO | 2017/062619 | 4/2017 |
| WO | 2017180813 A1 | 10/2017 |
| WO | 2017/189959 | 11/2017 |
| WO | 2017214335 A1 | 12/2017 |
| WO | 2018023025 A1 | 2/2018 |
| WO | 2018177393 A1 | 10/2018 |

OTHER PUBLICATIONS

PCT Search Report and Written Opinion, PCT Appl. No. PCT/US2019/061887, dated Feb. 10, 2020, 12 pages.
Ahmed, et al. "Humanized Affinity-matured Monoclonal Antibody 8H9 Potent Antitumor Activity and Binds to FG Loop of Tumor Antigen B7-H3," J. Biol. Chem., Dec. 11, 2015, vol. 290, No. 50, pp. 30018-30029.
Chen, et al. "Cloning and Characterization of Porcine 41g-B7-H3: A Potent Inhibitor of Porcine T-Cell Activation," 9 pages, Jun. 2011, vol. 6, Issue 6.
EP Partial Search Report for Co-Pending EP Application No. 19885550.4, dated Jul. 12, 2022, 15 pages.
EP Extended Search Report for Co-Pending EP Application No. 19885550.4, dated Oct. 13, 2022, 14 pages.
Baral et al. "B7-H3 and B7-H1 expression in cerebral spinal fluid and tumor tissue correlates with the malignancy grade of glioma patients" Oncol Lett 8: pp. 1195-1201 (2014).

(Continued)

*Primary Examiner* — Sean E Aeder
(74) *Attorney, Agent, or Firm* — Perkins Coie LLP

(57) ABSTRACT

The present disclosure provides monoclonal antibodies that bind to an IgV domain of human B7-H3. Also provided are methods of using these antibodies in treating cancer and infection and in imaging B7-H3 positive cells.

13 Claims, 4 Drawing Sheets
Specification includes a Sequence Listing.

(56) References Cited

OTHER PUBLICATIONS

Bird et al. "Single-Chain Antigen-Binding Proteins" Science, 242: 423-426 (1988).
Brentjens et al. Genetically targeted T cells eradicate systemic acute lymphoblastic leukemia xenografts. Clin Cancer Res 13(18 Pt 1):5426-5435 (2007).
Brown et al. "Tumor-specific Genetically Engineered Murine/Human Chimeric Monoclonal Antibody" Cancer Res. 47: 3577-3583 (1987).
Chen et al. The coexpression and clinical significance of costimulatory molecules B7-H1, B7-H3, and B7-H4 in human pancreatic cancer. Onco Targets Ther 7:1465-1472 (2014).
Chothia et al. "Conformations of immunoglobulin hypervariable regions" Nature 342:878-883 (1989).
Chothia, C. et al. "Canonical Structures for the Hypervariable Regions of Immunoglobulins" J. Mol. Biol. 196:901-917 (1987).
Daugherty et al. "Polymerase chain reaction facilitates the cloning, CDR-grafting, and rapid expression of a murine monoclonal antibody directed against the CD18 component of leukocyte integrins" Nucl. Acids Res. 19: 2471-2476 (1991).
Dossett et al. Adoptive immunotherapy of disseminated leukemia with TCR-transduced, CD8+ T cells expressing a known endogenous TCR. Mol Ther 17(4):742-749 (2009).
Dunbar et al. "ANARCI: antigen receptor numbering and receptor classification" Bioinformatics 15: 298-300 (2016).
Floros & Tarhini. Anticancer Cytokines: Biology and Clinical Effects of Interferon-a2, Interleukin (IL)-2, IL-15, IL-21, and IL-12. Semin Oncol 42(4):539-548 (2015).
Green et al. "Mitochondria and Apoptosis" Science 281: 1309 (1998).
Guest et al. The role of extracellular spacer regions in the optimal design of chimeric immune receptors: evaluation of four different scFvs and antigens. J Immunother 28(3):203-211 (2005).
Hamers-Casterman et al. "Naturally occurring antibodies devoid of light chains" Nature 363:446-448 (1993).
Harris & Kranz. Adoptive T Cell Therapies: A Comparison of T Cell Receptors and Chimeric Antigen Receptors. Trends Pharmacol Sci 37(3):220-230 (2016).
Harris, W.J. "Production of humanized monoclonal antibodies for in vivo imaging and therapy" Biochem. Soc. Transactions 23:1035-1038 (1995).
Hu et al. Expression of costimulatory molecule B7-H3 and its prognostic implications in human acute leukemia. Hematology 20:187-195 (2015).
Hurle, M. et al. "Protein engineering techniques for antibody humanization" Curr. Op. Biotech. 5:428-433 (1994).
Huston et al. "Protein engineering of antibody binding sites: Recovery of specific activity in an anti-digoxin single-chain Fv analogue produced in *Escherichia coli*" Proc. Natl. Acad. Sci. USA 85:5879-5883 (1988).
Ingebrigtsen et al. B7-H3 expression in colorectal cancer: associations with clinicopathological parameters and patient outcome. BMC Cancer 14:602 (2014).
Johnson and Wu "The Kabat Database and a Bioinformatics Example" Methods in Molecular Biology 248:1-25 (Lo, ed., Human Press, Totowa, N.J., 2003).
Jones et al., "Replacing the complementarity-determining regions in a human antibody with those from a mouse" Nature 321:522-525 (1986).
Kuball et al. Facilitating matched pairing and expression of TCR chains introduced into human T cells. Blood 109(6):2331-2338 (2007).
Leen et al. Improving T cell therapy for cancer. Annu Rev Immunol 25:243-265 (2007).
Lobuglio et al. "Mouse/human chimeric monoclonal antibody in man: Kinetics and immune response" Proc. Nat. Acad. Sci. USA 86: 4220-4224 (1989).
Patel et al. Impact of chimeric immune receptor extracellular protein domains on T cell function. Gene Therapy 6(3):412-419 (1999).

PCT Search Report and Written Opinion for PCT Application No. PCT/US2020/066002 issued Mar. 22, 2021. 9 pages.
Picarda et al. Molecular Pathways: Targeting B7-H3 (CD276) for Human Cancer Immunotherapy. Clin Cancer Res 22:3425-3431 (2016).
Presta, L. "Antibody Engineering" Current Opinion in Structural Biology, 2:593-596 (1992).
Qin et al. B7-H3 is a new cancer-specific endothelial marker in clear cell renal cell carcinoma. Onco Targets Ther 6:1667-1673 (2013).
Riechmann et al. "Reshaping human antibodies for therapy" Nature 332:323-327 (1988).
Sadelain et al. The basic principles of chimeric antigen receptor design. Cancer Discov 3(4):388-398 (2013).
Scatchard et al. "The Attractions of Proteins for Small Molecules and Ions" Annals of the New York Academy of Sciences, 51:660 (1949).
Schmitt et al. T cell receptor gene therapy for cancer. Hum Gene Ther 20(11):1240-1248 (2009).
Scholten et al. Codon modification of T cell receptors allows enhanced functional expression in transgenic human T cells. Clin Immunol 119(2):135-145 (2006).
Shaw et al. "Characterization of a mouse/human chimeric monoclonal antibody (17-1A) to a colon cancer tumor-associated antigen" J. Immunol. 138: 4534-4538 (1987),.
Sheriff et al. "Redefining the minimal antigen-binding fragment" Nature Struct. Biol. 3:733-736 (1996).
Stone et al. A novel T cell receptor single-chain signaling complex mediates antigen-specific T cell activity and tumor control. Cancer Immunol Immunother 63(11):1163-1176 (2014).
Sun et al. B7-H3 and B7-H4 expression in non-small-cell lung cancer. Lung Cancer 53:143-151 (2006).
Sun et al. B7-H3 expression in breast cancer and upregulation of VEGF through gene silence. Onco Targets Ther 7:1979-1986 (2014).
Sun et al. B7-H3 is expressed in human hepatocellular carcinoma and is associated with tumor aggressiveness and postoperative recurrence. Cancer Immunol Immunother 61:2171-2182 (2012).
Till et al. Adoptive immunotherapy for indolent non-Hodgkin lymphoma and mantle cell lymphoma using genetically modified autologous CD20-specific T cells. Blood 112(6):2261-2271 (2008).
Vaswami, S. et al. "Humanized antibodies as potential therapeutic drugs" Annals of Allergy, Asthma & Immunol. 1:105-115 (1998).
Verhoeyen et al. "Reshaping Human Antibodies: Grafting an Antilysozyme Activity" Science 239: 1534-1536 (1988).
Vigdorovich et al. Structure and T cell inhibition properties of B7 family member, B7-H3. Structure 21:707-717 (2013).
Walseng et al. A TCR-based Chimeric Antigen Receptor. Sci Rep 7(1):10713 (2017).
Wang et al. B7-H3 associated with tumor progression and epigenetic regulatory activity in cutaneous melanoma. J Invest Dermatol 133:2050-2058 (2013).
Wang et al. B7-H3 is overexpressed in patients suffering osteosarcoma and associated with tumor aggressiveness and metastasis. PLoS One 8:e70689 (2013).
Wang et al. Optimizing adoptive polyclonal T cell immunotherapy of lymphomas, using a chimeric T cell receptor possessing CD28 and CD137 costimulatory domains. Hum Gene Ther 18:712-725 (2007).
Ward et al. "Binding activities of a repertoire of single immunoglobulin variable domains secreted from *Escherichia coli*" Nature 341:544-546 (1989).
Wilson. Tech.Sight. Analyzing biomolecular interactions. Science 295(5562):2103-2105 (2002).
Winter et al. "Man-made antibodies" Nature 349: 293-299 (1991).
Wolff et al. Monoclonal antibody homodimers: enhanced antitumor activity in nude mice. Cancer Res 53(11):2560-2565 (1993).
Xu et al. "Diversity in the CDR3 Region of VH is Sufficient for Most Antibody Specificities" Immunity 13:37-45 (2000).
Xylinas et al. Association of T-cell co-regulatory protein expression with clinical outcomes following radical cystectomy for urothelial carcinoma of the bladder. Eur J Surg Oncol 40:121-127 (2014).
Zang & Allison. The B7 family and cancer therapy: costimulation and coinhibition. Clin Cancer Res 13:5271-5279 (2007).

(56) References Cited

OTHER PUBLICATIONS

Zang et al. B7-H3 and B7x are highly expressed in human prostate cancer and associated with disease spread and poor outcome. Proc Natl Acad Sci USA 104:19458-19463 (2007).

Zang et al. Tumor associated endothelial expression of B7-H3 predicts survival in ovarian carcinomas. Mod Pathol 23:1104-1112 (2010).

Zhao et al. HHLA2 is a member of the B7 family and inhibits human CD4 and CD8 T-cell function. Proc Natl Acad Sci USA 110:9879-9884 (2013).

Office Action for Japanese Application No. 2021-526660; Date of Mailing: Oct. 10, 2023; 8 pages.

* cited by examiner

MONOCLONAL ANTIBODIES AGAINST IgV DOMAIN OF B7-H3 AND USES THEREOF

CROSS-REFERENCE TO RELATED APPLICATION

This application is a continuation of International Patent Application No. PCT/US2019/061887, filed Nov. 15, 2019, which claims the benefit of U.S. Provisional Patent Application No. 62/768,128, filed on Nov. 16, 2018, the contents of which are herein incorporated by reference in their entirety into the present application.

SEQUENCE LISTING

The instant application contains a Sequence Listing which has been submitted electronically in ASCII format and is hereby incorporated by reference in its entirety. Said ASCII copy, created on May 7, 2021, is named SequenceListing.txt and is 18 MB in size.

BACKGROUND OF THE INVENTION

Throughout this application, various publications are referred to in parentheses. Full citations for these references may be found at the end of the specification. The disclosures of these publications are hereby incorporated by reference in their entirety into the subject application to more fully describe the art to which the subject invention pertains.

B7-H3 is a type I transmembrane protein and belongs to the B7 family. B7-H3 is overexpressed in human malignancies (1,2) including prostate cancer (3), liver cancer (4), melanoma (5), leukemia (6), breast cancer (7), ovarian cancer (8), pancreatic cancer (9), colorectal cancer (10), lung cancer (11), bladder cancer (12), renal cancer (13), brain cancer (14), and osteosarcoma (15). Several studies have correlated high B7-H3 expression levels with poor prognosis (1,2). These studies suggest that B7-H3 is an immune checkpoint used by human cancer cells to inhibit functions of immune cells (1,2). The extracellular part of B7-H3 is composed of IgV-IgC-IgV-IgC or IgV-IgC. Previous studies showed that the FG loop of the IgV domain of B7-H3 plays a critical role in B7-H3-mediated T cell suppression (16).

Cancers and infection are serious public health problems in the U.S. and other countries. The present invention provides antibodies that may be used in treating these diseases.

SUMMARY OF THE INVENTION

The present disclosure provides a monoclonal antibody or an antigen-binding fragment thereof that specifically binds to an IgV domain of a human B7-H3.

In some embodiments, the antibody comprises (a) a heavy chain having complementarity determining region (CDR) 1 comprising GYTFTSYWIT (SEQ ID NO:1), CDR2 comprising DIYPGSGSTNYNEKFKS (SEQ ID NO:2), and/or HCDR3 comprising ARGGTRFSPFAY (SEQ ID NO:3) (CDR3); and/or (b) a light chain having CDR (CDR) 1 comprising RSSQSIVHSNGNTYLE (SEQ ID NO:4), CDR2 comprising KVSNRFS (SEQ ID NO:5), and/or CDR3 comprising FQGSHVPWT (SEQ ID NO:6). In further embodiments, the antibody comprises a heavy chain variable domain (VH) and/or a light chain variable domain (VL) comprising amino acid sequences set forth in SEQ ID NOs: 14 and 16, respectively, without the leader sequences.

In some embodiments, the antibody comprises (a) a heavy chain having CDR1 comprising GYTFTSYWMH (SEQ ID NO:7), CDR2 comprising MIHPNSGSTNYNEKFKS (SEQ ID NO:8), and/or CDR3 comprising YYYGSSYAMDY (SEQ ID NO:9) (CDR3); and/or (b) a light chain having CDR1 comprising SASSSVSYMH (SEQ ID NO:10), CDR2 comprising STSNLAS (SEQ ID NO:11), and/or CDR3 comprising QQRSSYPYT (SEQ ID NO:12). In further embodiments, the antibody comprises a VH and/or a VL comprising amino acid sequences set forth in SEQ ID NOs: 18 and 20, respectively, without the leader sequences.

In some embodiments, the antibody comprises (a) a heavy chain having CDR1 comprising GYTFTSYWMH (SEQ ID NO:7); CDR2 comprising MIHPNSGSTNYNEKFKS (SEQ ID NO:8), and/or CRD3 comprising YYGTNV (SEQ ID NO:15); and/or (b) a light chain having CDR1 comprising KSVSTSGYSYMH (SEQ ID NO:13), CDR2 comprising LVSNLES (SEQ ID NO:14), and/or CDR3 comprising QHIREAYT (SEQ ID NO:16). In further embodiments, the antibody comprises a VH and/or VL comprising amino acid sequences set forth in SEQ ID NOS: 23 and 25, respectively, without the leader sequences.

In some embodiments, the antibody competes with the above antibody or a fragment thereof for binding to the IgV domain of human B7-H3.

In certain embodiments, the antibody is a humanized antibody or a chimeric antibody.

Also provided are uses of the antibody or fragment for treating cancers and infections and imaging B7-H3 positive cells.

DETAILED DESCRIPTION OF THE INVENTION

Figure 1A:
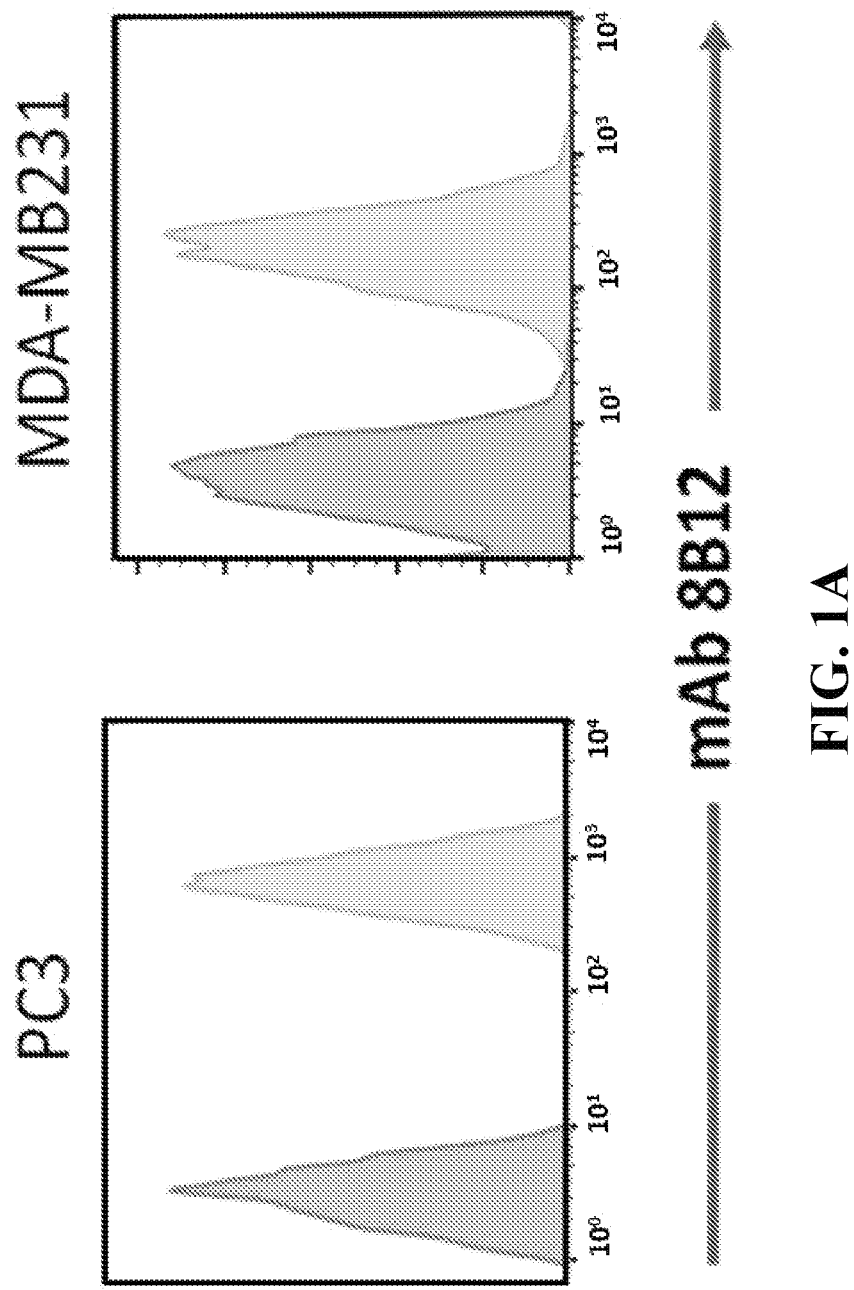
FIGS. 1A-1B. FACS shows that mAb 8B12 (FIG. 1A) and 12B4 (FIG. 1B) bind to endogenous B7-H3 expressed by human cancer lines PC3 (left) and MDA-MB231 (right). 8B12 or 12B4 SOBS (right histograms in each pair) or mouse IgG isotype controls (left histograms in each pair).

The invention provides a monoclonal antibody or an antigen-binding fragment thereof that binds to an IgV domain of a human B7-H3, comprising:
I) a) a heavy chain comprising one or more of:
  GYTFTSYWIT (SEQ ID NO:1) (complementarity determining region (CDR), CDR1), or
  DIYPGSGSTNYNEKFKS (SEQ ID NO:2) (CDR2), or
  ARGGTRFSPFAY (SEQ ID NO:3) (CDR3); and
  b) a light chain comprising one or more of:
  RSSQSIVHSNGNTYLE (SEQ ID NO:4) (CDR1), or
  KVSNRFS (SEQ ID NO:5) (CDR2), or
  FQGSHVPWT (SEQ ID NO:6) (CDR3); or
II) a) a heavy chain comprising one or more of:
  GYTFTSYWMH (SEQ ID NO:7) (CDR1), or
  MIHPNSGSTNYNEKFKS (SEQ ID NO:8) (CDR2), or
  YYYGSSYAMDY (SEQ ID NO:9) (CDR3); and b) a light chain comprising one or more of:
SASSSVSYMH (SEQ ID NO:10) (CDR1), or
STSNLAS (SEQ ID NO:11) (CDR2), or
QQRSSYPYT (SEQ ID NO:12) (CDR3); or
III) an antibody or fragment thereof that competes with the antibody or fragment of I) or II) for binding to the IgV domain of human B7-H3.

The B7-H3 IgV domain-binding fragment can be, for example, a Fab, F(ab)2, or scFv fragment.

In some embodiments, the antibody or fragment comprises
a heavy chain comprising

```
                (CDR1)
                                        (SEQ ID NO: 1)
    GYTFTSYWIT, (CDR2)
                                        (SEQ ID NO: 2)
    DIYPGSGSTNYNEKFKS,
    and (CDR3)
                                        (SEQ ID NO: 3)
    ARGGTRFSPFAY;
``` and
a light chain comprising

```
                (CDR1)
                                        (SEQ ID NO: 4)
    RSSQSIVHSNGNTYLE, (CDR2)
                                        (SEQ ID NO: 5)
    KVSNRFS,
    and (CDR3)
                                        (SEQ ID NO: 6)
    FQGSHVPWT.
```

In some embodiments, the antibody or fragment comprises
a) a heavy chain comprising

```
                (CDR1)
                                        (SEQ ID NO: 7)
    GYTFTSYWMH, (CDR2)
                                        (SEQ ID NO: 8)
    MIHPNSGSTNYNEKFKS,
    and (CDR3)
                                        (SEQ ID NO: 9)
    YYYGSSYAMDY;
``` and
b) a light chain comprising

```
                (CDR1)
                                        (SEQ ID NO: 10)
    SASSSVSYMH, (CDR2)
                                        (SEQ ID NO: 11)
    STSNLAS,
    and
```

```
                (CDR3)
                                        (SEQ ID NO: 12)
    QQRSSYPYT.
```

In certain embodiments, the framework regions of the light chain and the heavy chain are human framework regions, or have 85%, 90%, 95%, 96%, 97%, 98%, or 99% or more identity thereto. In certain embodiments, the anti-B7-H3 antibody or B7-H3-binding fragment thereof comprises (i) a VH framework comprising the framework sequence of human germline IGHV1-46*01, IGHV1-46*02, IGHV1-46*03, IGHD1-1*01, IGHD1-26*01, IGHD2-8*01, IGHD3-10*01, IGHD3-22*01, IGHD4-23*01, IGHJ3*01, IGHJ4*01, IGHJ4*03, IGHJ6*01, or IGHJ6*02; and/or (ii) a VL framework comprising the framework sequence of human germline IGKV2-18*01, IGKV2D-29*02, IGKV2-29*03, IGKV3-11*01, IGKV3-15*01, IGKV3-20*02, IGKJ1*01, IGKJ2*01, IGKJ4*01, or IGKJ4*02.

In certain embodiments, the antibody or fragment has a human heavy chain constant domain, e.g., a human Fc region. In some embodiments, the human heavy chain constant domain is derived from a human IgG, such as IgG1, IgG2, IgG3, or IgG4. In some embodiments, the antibody or fragment comprises a human kappa light chain constant domain.

In particular embodiments, the antibody or fragment is a blocking antibody or fragment, or an inhibitory antibody or fragment and it antagonizes a biological activity of B7-H3.

Also provided is a bispecific antibody comprising an antigen-binding domain of any of the anti-B7-H3 antibodies described herein, and an antigen-binding domain of a monoclonal antibody that binds to a CD3 component of a T-cell receptor (TCR) complex on T cells.

Also provided is an isolated nucleic acid or cDNA encoding a complementarity determining region of an anti-B7-H3 antibody that comprises one or more of:

```
            (heavy chain CDR1)
                                        (SEQ ID NO: 1)
    GYTFTSYWIT, (heavy chain CDR2)
                                        (SEQ ID NO: 2)
    DIYPGSGSTNYNEKFKS, (heavy chain CDR3)
                                        (SEQ ID NO: 3)
    ARGGTRFSPFAY, (light chain CDR1)
                                        (SEQ ID NO: 4)
    RSSQSIVHSNGNTYLE, (light chain CDR2)
                                        (SEQ ID NO: 5)
    KVSNRFS,
    and (light chain CDR3)
                                        (SEQ ID NO: 6)
    FQGSHVPWT.
```

Also provided is an isolated nucleic acid or cDNA encoding a complementarity determining region of an anti-B7-H3 antibody that comprises one or more of:

```
            (heavy chain CDR1)
                                        (SEQ ID NO: 7)
    GYTFTSYWMH,
```

```
              (heavy chain CDR2)
                             (SEQ ID NO: 8)
              MIHPNSGSTNYNEKFKS, (heavy chain CDR3)
                             (SEQ ID NO: 9)
              YYYGSSYAMDY, (light chain CDR1)
                             (SEQ ID NO: 10)
              SASSSVSYMH, (light chain CDR2)
                             (SEQ ID NO: 11)
              STSNLAS,
              and (light chain CDR3)
                             (SEQ ID NO: 12)
              QQRSSYPYT.
```

Also provided is an isolated nucleic acid or cDNA encoding a complementarity determining region of an anti-B7-H3 antibody that comprises one or more of:

```
              (heavy chain CDR1)
                             (SEQ ID NO: 7)
              GYTFTSYWMH, (light chain CDR1)
                             (SEQ ID NO: 13)
              KSVSTSGYSYMH, (heavy chain CDR2)
                             (SEQ ID NO: 8)
              MIHPNSGSTNYNEKFKS, (light chain CDR2)
                             (SEQ ID NO: 14)
              LVSNLES, (heavy chain CDR3)
                             (SEQ ID NO: 15)
              YYGTNV,
              and (light chain CDR3)
                             (SEQ ID NO: 16)
              QHIREAYT.
```

In any of the above embodiments, the nucleic acids may be isolated. Nucleic acids referred to herein as "isolated" or "purified" are nucleic acids which (1) have been separated away from the nucleic acids of the genomic DNA or cellular RNA of their source of origin; and/or (2) do not occur in nature.

Also provided is a vector or host cell comprising the isolated nucleic acid (e.g., cDNA).

Also provided is method of producing an anti-B7-H3 IgV domain antibody or B7-H3 IgV domain-binding fragment thereof, comprising culturing the host cell described herein, under conditions wherein the anti-B7-H3 IgV domain antibody or B7-H3 IgV domain-binding fragment is produced by the host cell.

Still further provided is a pharmacological composition comprising any of the antibodies or fragments thereof disclosed herein, and a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution.

Compositions or pharmaceutical compositions comprising the antibodies or fragments of antibodies disclosed herein preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars that can contribute to overcoming aggregation problems. Where a composition or pharmaceutical composition of the present invention is used as an injection, it is desirable to have a pH value in an approximately neutral pH range. It is also advantageous to minimize surfactant levels to avoid bubbles in the formulation which are detrimental for injection into subjects. In some embodiments, the composition or pharmaceutical composition is in liquid form and stably supports high concentrations of bioactive antibody in solution and is suitable for inhalational or parenteral administration.

The pharmaceutically acceptable carrier used can depend on the route of administration. The pharmaceutical composition can be formulated for administration by any method known in the art. In some embodiments, the composition or pharmaceutical composition is suitable for intravenous, intramuscular, intraperitoneal, intradermal and/or subcutaneous injection. In some embodiments, the composition or pharmaceutical composition is in liquid form and has minimized risk of bubble formation and anaphylactoid side effects. In some embodiments, the composition or pharmaceutical composition is isotonic. In some embodiments, the composition or pharmaceutical composition has a pH of 6.8 to 7.4.

The invention also provides a method of enhancing immune function in a subject comprising administering to the subject any of the antibodies or fragments thereof disclosed herein in an amount effective to enhance immune function in a subject. The subject can have, for example, cancer or an infection.

The invention further provides a method of treating cancer in a subject comprising administering to the subject any of the antibodies or fragments thereof disclosed herein in an amount effective to treat cancer in a subject. The cancer can be, for example, prostate cancer, liver cancer, melanoma, leukemia, breast cancer, ovarian cancer, pancreatic cancer, colorectal cancer, lung cancer, bladder cancer, renal cancer, brain cancer or osteosarcoma, Adrenal Cancer, Anal Cancer, Basal and Squamous Cell Skin Cancer, Bile Duct Cancer, Bladder Cancer, Bone Cancer, Brain and Spinal Cord Tumors, Breast Cancer, Cervical Cancer, Colorectal Cancer, Endometrial Cancer, Esophagus Cancer, Ewing Family of Tumors, Eye Cancer (Ocular Melanoma), Gallbladder Cancer, Gastrointestinal Neuroendocrine (Carcinoid) Tumors, Gastrointestinal Stromal Tumor (GIST), Gestational Trophoblastic Disease, Kaposi Sarcoma, Kidney Cancer, Laryngeal and Hypopharyngeal Cancer, Liver Cancer, Lung Cancer, Lung Carcinoid Tumor, Malignant Mesothelioma, Melanoma Skin Cancer, Merkel Cell Skin Cancer, Nasal Cavity and Paranasal Sinuses Cancer, Nasopharyngeal Cancer, Neuroblastoma, Non-Small Cell Lung Cancer, neoplasm of the central nervous system (CNS), Oral Cavity and Oropharyngeal Cancer, Osteosarcoma, Ovarian Cancer, Pancreatic Cancer, Pancreatic Neuroendocrine Tumor (NET), Penile Cancer, Pituitary Tumors, Prostate Cancer, Retinoblastoma, Rhabdomyosarcoma, Salivary Gland Cancer, Skin Cancer, Small Cell Lung Cancer, Small Intestine Cancer, Soft Tissue Sarcoma, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor, squamous cell cancer, environmentally induced cancers, combinations of the cancers, metastatic lesions of cancers, myeloid neoplasm, acute myeloid leukemia (AML), AML with recurrent genetic abnormalities, AML with myelodysplasia-related changes, therapy-related AML, acute leukemias of ambiguous lineage, myeloproliferative neoplasm, essential thrombocythemia, polycythemia vera, myelofibrosis (MF), primary myelofibrosis, systemic mastocytosis, myelodysplastic syndromes (MDS), myeloproliferative/myelodysplastic syndromes, chronic myeloid leukemia, chronic neutrophilic leukemia, chronic eosinophilic leukemia, myelodysplastic syndromes (MDS), refractory anemia with ringed sideroblasts, refractory cytopenia with multilineage dysplasia, refractory anemia with excess blasts (type 1), refractory anemia with excess blasts (type 2), MDS with isolated del (5q), unclassifiable MDS, myeloproliferative/myelodysplastic syndromes, chronic myelomonocytic leukemia, atypical chronic myeloid leukemia, juvenile myelomonocytic leukemia, unclassifiable myeloproliferative/myelodysplatic syndromes, lymphoid neoplasms, precursor lymphoid neoplasms, B lymphoblastic leukemia, B lymphoblastic lymphoma, T lymphoblastic leukemia, T lymphoblastic lymphoma, mature B-cell neoplasms, diffuse large B-cell lymphoma, primary central nervous system lymphoma, primary mediastinal B-cell lymphoma, Burkitt lymphoma/leukemia, follicular lymphoma, chronic lymphocytic leukemia, small lymphocytic lymphoma, B-cell prolymphocytic leukemia, lymphoplasmacytic lymphoma, Waldenstrom macroglobulinemia, mantle cell lymphoma, marginal zone lymphomas, post-transplant lymphoproliferative disorders, HIV-associated lymphomas, primary effusion lymphoma, intravascular large B-cell lymphoma, primary cutaneous B-cell lymphoma, hairy cell leukemia, multiple myeloma, monoclonal gammopathy of unknown significance (MGUS), smoldering multiple myeloma, or solitary plasmacytomas (solitary bone and extramedullary). The cancer may be, e.g., at an early, intermediate, late, locally advanced, or metastatic stage, and may be relapsed or refractory to other therapeutics or there may be no standard therapy available. As used herein, to "treat" a cancer means to reduce the number of cancer cells or metastases in an organ or tissue, and/or to delay growth of a tumor, and/or to kill tumor cells, metastatic tumor cells or tumor cells that are likely to metastasize, and/or to prevent or reduce the spread of cancerous cells from an original site in the body to another site in the body, and/or to inhibit the progression of metastatic cancer, and/or to prevent the reoccurrence of metastasis, and/or to slow or decrease disease progression, and/or to increase survival.

The invention further provides a method of treating an infection in a subject comprising administering to the subject any of the antibodies or fragments thereof disclosed herein in an amount effective to treat an infection in a subject. The infection can be caused, for example, by a virus, viroid, bacterium, prion, nematode, arthropod, fungus or protozoa. As used herein, to "treat" an infection means to reduce a sign or symptom of the infection and/or to reduce the number of infectious pathogens in a subject.

The present disclosure invention also contemplates the use of sequences (e.g., the six CDR or VH and VL sequences) of an antibody or fragment described herein in the preparation of a chimeric antigen receptor, which may be for use in CAR-T technology.

It is understood that the antibodies and fragments thereof, compositions, and bi-specific binding molecules of the present invention may be used in a method of treatment as described herein, may be for use in a treatment as described herein, and/or may be for use in the manufacture of a medicament for a treatment as described herein. The present invention also provides kits and articles of manufacture comprising the antibodies and antigen-binding portions thereof, compositions, and bi-specific binding molecules described herein.

Any of the anti-B7-H3 antibodies or fragments thereof disclosed herein can further comprise a detectable marker conjugated thereto, such as a fluorescent or radioactive label. Also provided is a method of detecting B7-H3 positive cells in a subject comprising administering the antibody or fragment (e.g., labeled with a detectable marker) to the subject in an amount effective to bind detectably to B7-H3 positive cells, and then detecting the presence of the antibody or fragment in the subject, thereby detecting B7-H3 positive cells in the subject. A label can be detected, for example, by imaging. The B7-H3 positive cells can be, for example, cancer cells.

Any of the anti-B7-H3 antibodies or fragments thereof disclosed herein can further be included in an antibody-drug conjugate ("ADC"). ADC compositions according to the present disclosure may include an antibody or fragment thereof according to the present disclosure in combination with, e.g., a cytotoxic agent and a linker. Cytotoxic agents that may be used include, but are not limited to, alkylating agents, bifunctional alkylators, monofunctional alkylators, anthracyclines, cytoskeletal disruptors, taxanes, epothilones, histone deacetylase inhibitors, topoisomerase I inhibitors, topoisomerase II inhibitors, kinase inhibitors, nucleotide analogs, nucleotide precursor analogs, peptide antibiotics, platinum-based agents, retinoids, vinca alkaloids and derivatives thereof, actinomycin, all-trans retinoic acid, azacytidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorothamine, mercaptopurine, methotrexate, mitoxantrone, oxaliplatin, paclitaxel, pemetrexed, teniposide, tioguanine, topotecan, valrubicin, vemurafenib, vinblastine, vincristine, or Fvindesine. ADCs according to the present disclosure may include an antibody or a fragment thereof according to the present disclosure linked (e.g., covalently) to a small molecule or a drug.

As used herein, the term "antibody" refers to an intact antibody, i.e., with complete Fc and Fv regions. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989). "Fragment" refers to any portion of an antibody, or portions of an antibody linked together, such as, in non-limiting examples, a Fab, F(ab)2, or a single-chain Fv (scFv), which is less than the whole antibody but which is an antigen-binding portion and which competes with the intact antibody of which it is a fragment for specific binding. In this case, the antigen is the human B7-H3 IgV domain. Such fragments can be prepared, for example, by cleaving an intact antibody or by recombinant means. See generally, Fundamental Immunology, Ch. 7 (Paul, W., ed., 2nd ed. Raven Press, N.Y. (1989)). Antigen-binding fragments may be produced by recombinant DNA techniques or by enzymatic or chemical cleavage of intact antibodies or by molecular biology techniques.

In some embodiments, a fragment is an Fab, Fab', F(ab')2, Fd, Fv, complementarity determining region (CDR) fragment, single-chain antibody (scFv), or a variable domain light chain (VL) and a variable domain heavy chain (VH) linked via a peptide linker, or a polypeptide that contains at least a portion of an antibody that is sufficient to confer human B7-H3 IgV domain specific antigen binding on the polypeptide, including a diabody. As used herein, an Fd fragment means an antibody fragment that consists of the VH and CH1 domains; an Fv fragment consists of the V1 and VH domains of a single arm of an antibody; and a dAb fragment (Ward et al., Nature 341:544-546 (1989) hereby incorporated by reference in its entirety) consists of a VH domain. In some embodiments, fragments are at least 5, 6, 8, or 10 amino acids long. In other embodiments, the fragments are at least 14, at least 20, at least 50, or at least 70, 80, 90, 100, 150, or 200 amino acids long.

In some embodiments, an scFv described herein comprises a variable domain framework sequence having a sequence identical to a human variable domain FR1, FR2, FR3 and/or FR4. In some embodiments, the scFv comprises a linker peptide from 5 to 30 amino acid residues long. In some embodiments, the scFv comprises a linker peptide comprising one or more of glycine, serine and threonine residues. In some embodiments, the linker of the scFv is 10-25 amino acids in length. In certain embodiments, the peptide linker comprises glycine, serine and/or threonine residues. For example, see Bird et al., Science, 242: 423-426 (1988) and Huston et al., Proc. Natl. Acad. Sci. USA, 85:5879-5883 (1988).

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a human B7-H3 IgV domain. In contrast to polyclonal antibody preparations, which typically include different antibodies directed against different determinants (epitopes), each antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified.

In some embodiments disclosed herein, the antibody or fragment is isolated. As used herein, the term "isolated antibody" or "isolated antigen-binding fragment" refers to an antibody or fragment that by virtue of its origin or source of derivation has one, two, three or four of the following properties: (1) is not associated with naturally associated components that accompany it in its native state, (2) is free of other proteins from the same species, (3) is expressed by a cell from a different species, and (4) does not occur in nature absent the hand of man.

In certain embodiments, the antibody is humanized. "Humanized" forms of non-human (e.g., murine) antibodies are chimeric antibodies that contain minimal sequence derived from non-human immunoglobulin. In some embodiments, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDRs (CDR1-3 of both the heavy and light chain) of the murine antibodies described herein. In certain embodiments, framework (FR) residues of the murine mAb are replaced with corresponding human immunoglobulin variable domain framework (FR) residues. These may be modified further in embodiments to further refine antibody performance. Furthermore, in particular embodiments, humanized antibodies may comprise residues that are not found in the recipient antibody or in the donor antibody. In some embodiments, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, both of which are hereby incorporated by reference in their entirety. In some embodiments where the humanized antibodies do comprise residues that are not found in the recipient antibody or in the donor antibody, the Fc regions of the antibodies may be modified as described in WO 99/58572, the content of which is hereby incorporated by reference in its entirety.

Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, all of which are hereby incorporated by reference in their entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, e.g., Winter et al. Nature 349: 293-299 (1991), Lobuglio et al. Proc. Nat. Acad. Sci. USA 86: 4220-4224 (1989); Shaw et al. J. Immunol. 138: 4534-4538 (1987); Brown et al. Cancer Res. 47: 3577-3583 (1987). Other references describe rodent hypervariable regions or CDRs grafted into a human supporting framework region (FR) prior to fusion with an appropriate human antibody constant domain. See, e.g., Riechmann et al., Nature 332: 323-327 (1988); Verhoeyen et al., Science 239: 1534-1536 (1988); Jones et al., Nature 321: 522-525 (1986). Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g., PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (all of which are incorporated by reference in their entirety).

In some embodiments, the antibodies or fragments herein can be produced recombinantly; for example, antibodies expressed using a recombinant expression vector transfected into a host cell, antibodies isolated from a recombinant, combinatorial human antibody library, antibodies isolated from an animal (e.g., a mouse) that is transgenic for human immunoglobulin genes, etc.

The term "$K_d$", as used herein, is intended to refer to the dissociation constant of an antibody-antigen interaction. The affinity constant is the inverted dissociation constant. One way of determining the $K_d$ or binding affinity of antibodies to the B7-H3 IgV domain is by measuring binding affinity of monofunctional Fab fragments of the antibody. To obtain monofunctional Fab fragments, an antibody (for example, IgG) can be cleaved with papain or expressed recombinantly. The affinity of a fragment of an anti-human B7-H3 IgV domain antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used (for example, ELISA).

An antibody or a polypeptide that "specifically binds" to an epitope is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a human B7-H3 IgV domain is an antibody that binds this epitope with greater affinity, avidity, more readily, and/or with greater duration than it binds to other B7-H3 epitopes or non-B7-H3 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. In some embodiments, an antibody is said to specifically bind to an antigen when the $K_d$ is ≤1 mM, preferably ≤100 nM.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In some embodiments the antibody is an immunoglobulin G. In some embodiments, the antibody fragment is a fragment of an immunoglobulin G. In some embodiments, the antibody is an IgG1, IgG2, IgG2a, IgG2b, IgG3 or IgG4. In some embodiments, the antibody comprises sequences from a human IgG1, human IgG2, human IgG2a, human IgG2b, human IgG3 or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domain of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions, and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (□) and lambda (□), based on the amino acid sequences of their constant domains.

"Framework" or "FR" residues are those variable domain residues other than the HVR residues as herein defined.

The term "hypervariable region" or "HVR" or "CDR" when used herein refers to the regions of an antibody variable domain which are hypervariable in sequence and/or form structurally defined loops. Generally, antibodies comprise six CDRs; three in the VH (H1, H2, H3) and three in the VL (L1, L2, L3). In native antibodies, H3 and L3 display the most diversity of the six CDRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of CDR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia refers instead to the location of the structural loops (Chothia and Lesk, J. Mol. Biol. 196:901-917 (1987)). The AbM CDRs represent a compromise between the Kabat CDRs and Chothia structural loops and are used by Oxford Molecular's AbM antibody modeling software. The "contact" CDRs are based on an analysis of the available complex crystal structures. CDRs may comprise "extended CDRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

The subject can be any mammal and is preferably a human.

In some embodiments, human B7-H3 has the following amino acid sequence (GenBank: CAE47548.1, SEQ ID NO:17), wherein the IgV domain is underlined:

```
  1  MLRRRGSPGM GVHVGAALGA LWFCLTGALE VQVPEDPVVA
     LVGTDATLCC SFSPEPGFSL

61  AQLNLIWQLT DTKQLVHSFA EGQDQGSAYA NRTALFPDLL
     AQGNASLRLQ RVRVADEGSF

121  TCFVSIRDFG SAAVSLQVAA PYSKPSMTLE PNKDLRPGDT
     VTITCSSYQG YPEAEVFWQD

181  GQGVPLTGNV TTSQMANEQG LFDVHSILRV VLGANGTYSC
     LVRNPVLQQD AHSSVTITPQ

241  RSPTGAVEVQ VPEDPVVALV GTDATLRCSF SPEPGFSLAQ
     LNLIWQLTDT KQLVHSFTEG
```

-continued

```
301  RDQGSAYANR TALFPDLLAQ GNASLRLQRV RVADEGSFTC
     FVSIRDFGSA AVSLQVAAPY

361  SKPSMTLEPN KDLRPGDTVT ITCSSYRGYP EAEVFWQDGQ
     GVPLTGNVTT SQMANEQGLF

421  DVHSVLRVVL GANGTYSCLV RNPVLQQDAH GSVTITGQPM
     TFPPEALWVT VGLSVCLIAL

481  LVALAFVCWR KIKQSCEEEN AGAEDQDGEG EGSKTALQPL
     KHSDSKEDDG QEIA.
```

"And/or" as used herein, for example, with option A and/or option B, encompasses the separate embodiments of (i) option A, (ii) option B, and (iii) option A plus option B.

All combinations of the various elements described herein, including all subsets, are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Generation of mAbs Against the IgV Domain of Human B7-H3 and Mouse B7-H3

As the IgV domain is the functional domain of B7-H3, human B7-H3 IgV-Ig fusion protein was generated by fusing the B7-H3 IgV coding region (E35-A139) to a human IgG1 Fc tag of plasmid pMT/BiP as previously described (17). The fusion protein was expressed in a S2 system and then purified. Mice were immunized with the B7-H3 IgV-Ig fusion protein, and hybridomas were generated by standard techniques from splenocytes fused to NSO myeloma cells.

Characterization of mAbs 8B12 and 12B4

Monoclonal antibodies (mAbs) 8B12 and 12B4 were generated. 8B12 is an IgG3 with a kappa light chain, whereas 12B4 is an IgG2b with a kappa light chain.

Figure 1B:
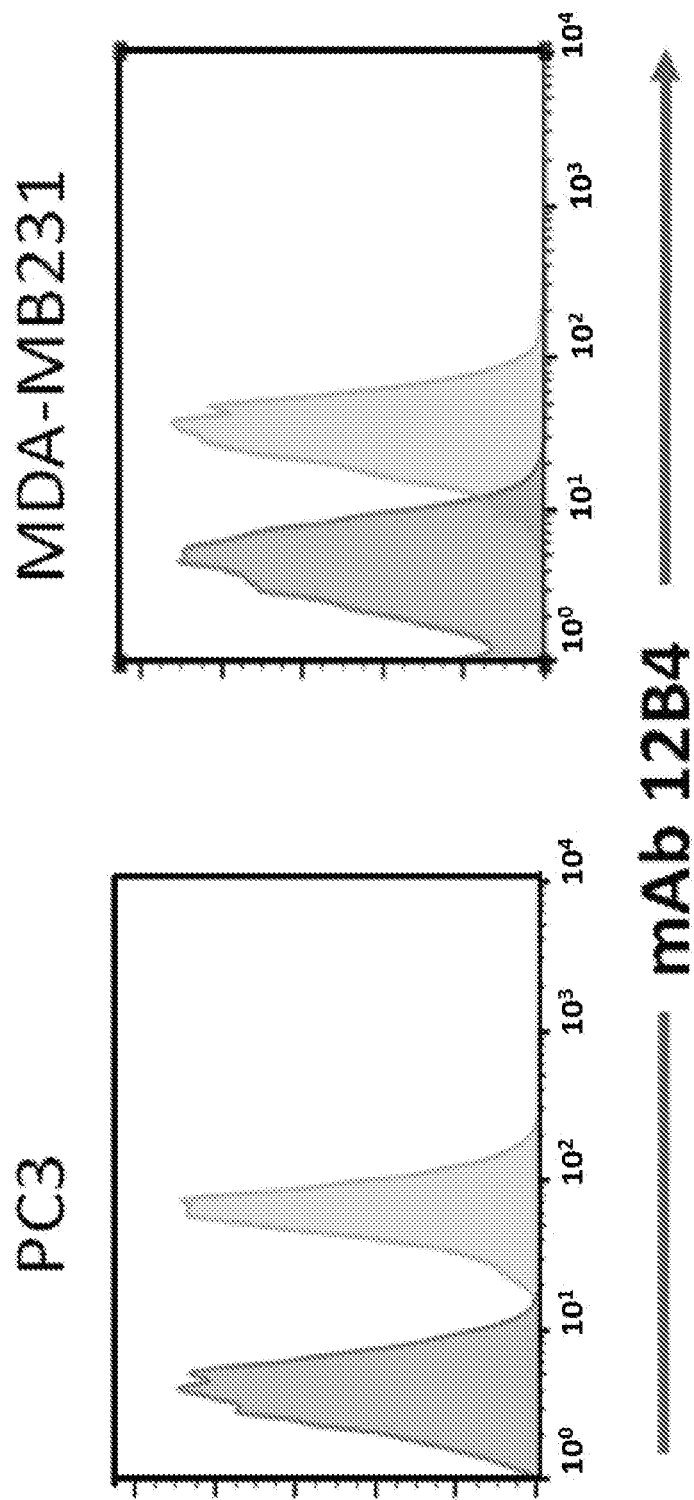

By the Surface Plasmon Resonance method, it was determined that the binding affinities ($K_d$) of mAb 8B12 for human B7-H3 and mouse B7-H3 was 0.30 nM and 4.01 nM, respectively, and that the binding affinities ($K_d$) of mAb 12B4 for human B7-H3 and mouse B7-H3 was 8.23 nM and 15.38 nM, respectively (Table 1). Both 8B12 and 12B4 strongly bound to endogenous B7-H3 expressed by human cancer lines PC3 and MDA-MB231 (FIG. 1).

Figure 2:
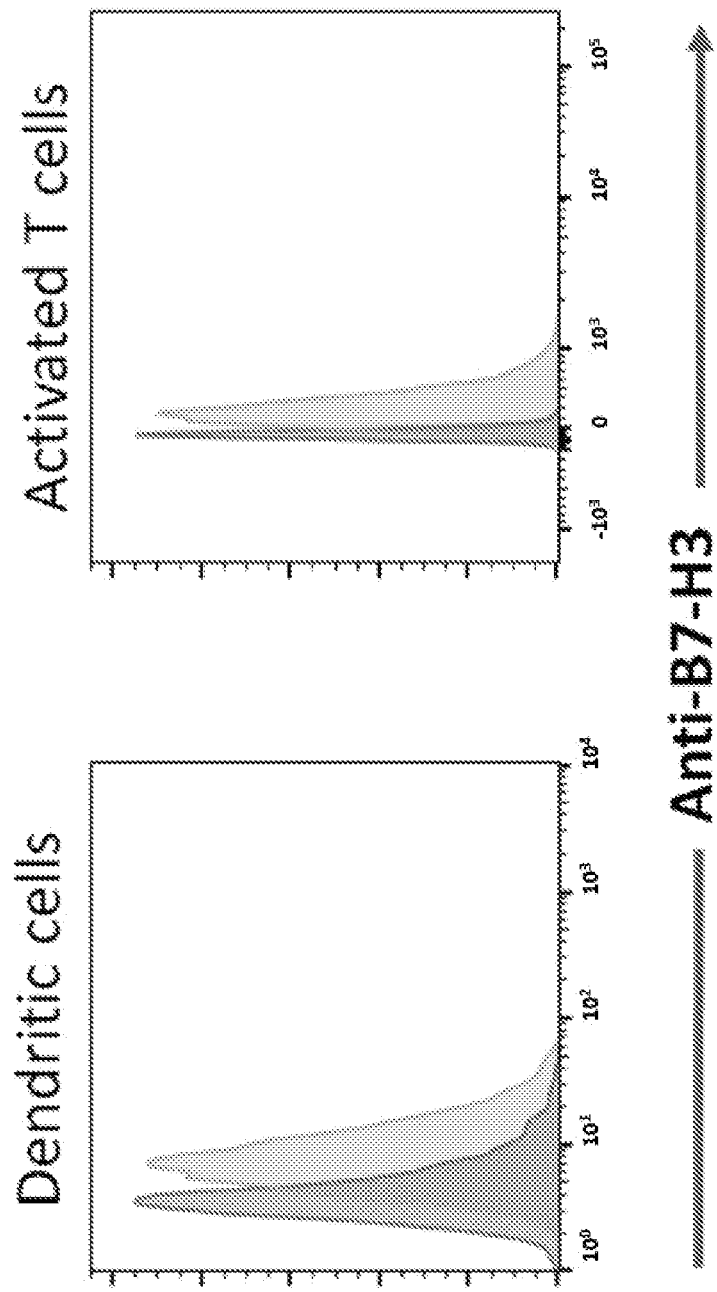
FIG. 2. FACS shows that both dendritic cells (left) and activated T cells (right) express B7-H3. A mAb against B7-H3 (right histograms in each pair) or mouse IgG isotype control (left histograms in each pair).
Figure 3A:
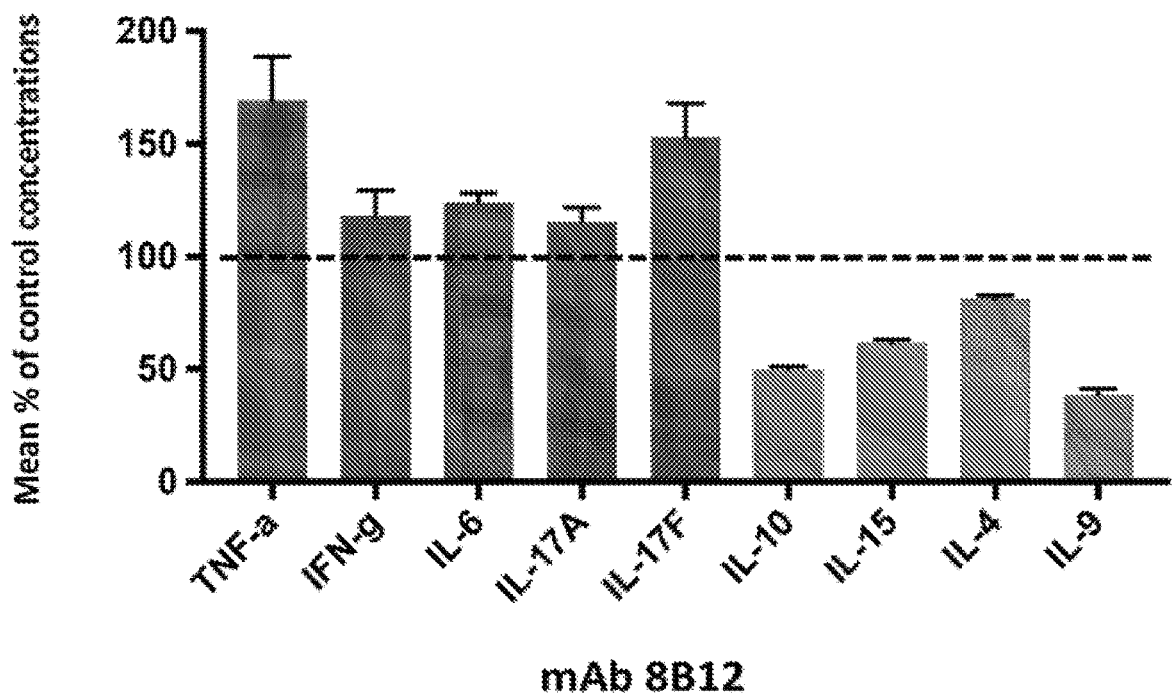
FIGS. 3A-3B. mAb 8B12 (FIG. 3A) and 12B4 (FIG. 3B) are able to regulate cytokine production from T cells in a mixed lymphocyte reaction assay. N=2-4.
Figure 3B:
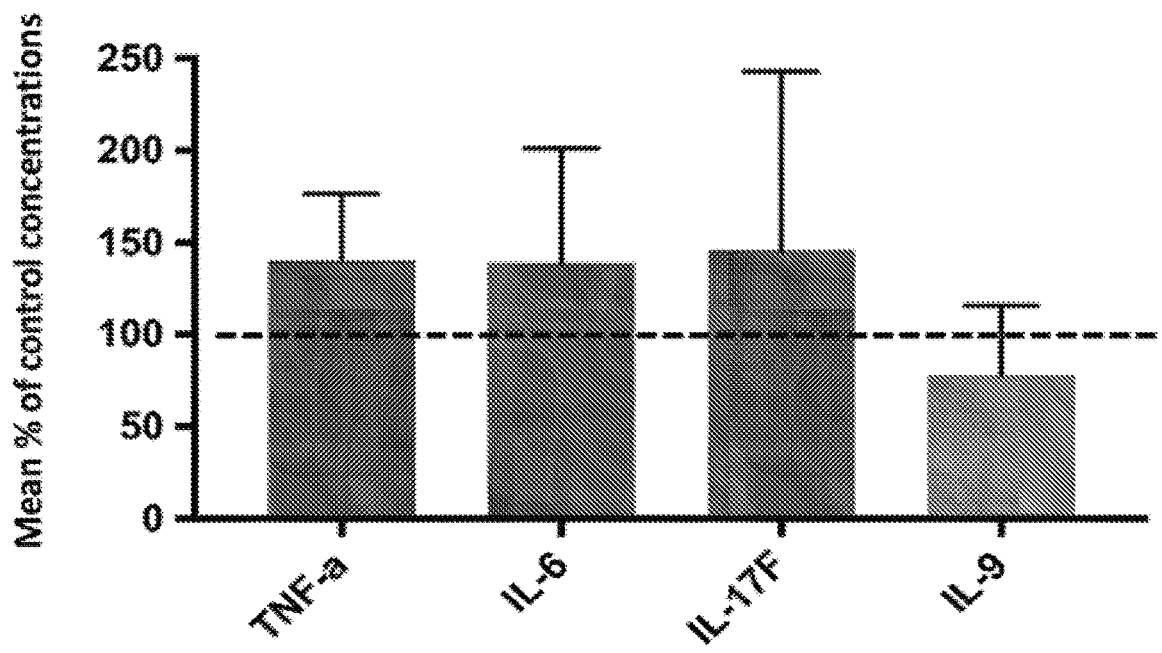

Since both dendritic cells and activated T cells express B7-H3 (FIG. 2), a mixed lymphocyte reaction was performed to determine the antagonistic activity of 8B12 and 12B4. Mature dendritic cells, which were differentiated from monocytes isolated from PBMC from one donor, were incubated with purified T cells, which were from PBMC from another donor, for four days in the presence of 8B12, 12B4, or control mouse IgG. 8B12 and 12B4 were able to regulate cytokine production by T cells (FIGS. 3A and 3B).

TABLE 1

Kinetic parameters from Surface Plasmon Resonance of 8B12, 12B4, and 24D12.

| mAb clone # | Isotype | Antigen | $K_{assoc}(Ms)^{-1}$ | $K_{dissoc}(s^{-1})$ | $K_d$ (nM) |
|---|---|---|---|---|---|
| 8B12 | IgG3, K | Human B7-H3 | $15.070 \times 10^5$ | $4.591 \times 10^{-4}$ | 0.30 |
| 8B12 | IgG3, K | Mouse B7-H3 | $5.916 \times 10^5$ | $23.74 \times 10^{-4}$ | 4.01 |
| 12B4 | IgG2b, K | Human B7-H3 | $6.178 \times 10^5$ | $50.85 \times 10^{-4}$ | 8.23 |
| 12B4 | IgG3, K | Mouse B7-H3 | $11.93 \times 10^5$ | $183.50 \times 10^{-4}$ | 15.38 |
| 24D12 | IgG3, K | Human B7-H3 | $8.066 \times 10^5$ | $45.35 \times 10^{-4}$ | 5.62 |
| 24D12 | IgG3, K | Mouse B7-H3 | $12.74 \times 10^5$ | $21.81 \times 10^{-4}$ | 1.70 |

Sequences of mAbs 8B12, 12B4, and 24D12

8B12 was sequenced and found to have unique VH and VL sequences. The polypeptide and coding sequences of 8B12 are listed below:

8B12 heavy chain VH: Leader sequence-FR1-CDR1-FR2-CDR2-FR3-CDR3-FR4 (Leader sequence bolded. CDRs1-3 underlined):
DNA sequence (419 bp; SEQ ID NO: 18)
ATGGAATGGAGCTGGGTCATCCTCATTTTGGTAGCAGCAGCTACAGGTGT

CCACTCCCAGGTCCAACTGCAGCAGCCTGGGGCTGAGCTTGTGAAGCCTG

GGGCTTCAGTGAAGATGTCCTGCAAGGCTTCT<u>GGCTACACCTTCACCAGC

TACTGGATAAAC</u>TGGGTGAAGCAGAGGCCTGGACAAGGCCTTGAGTGGAT

T<u>GGAGATATTTATCCTGGTAGTGGTAGTACTAACTACAATGAGAAGTTCA

AGAGC</u>AAGGCCACTCTGACTGTAGACACATCCTCCAGCACAGCCTACATG

CAGCTCAGCAGCCTGACATCTGAGGACTCTGCGGTCTATTACTGTGCAAG

A<u>GGGGGTACTAGATTCAGCCCCTTTGCTTACTGG</u>GGCCAAGGGACTCTGG

TCACTGTCTCTGCAGCTAC;

Amino acid sequence (139 aa; SEQ ID NO: 19)
MEWSWVILILVAAATGVHSQVQLQQPGAELVKPGASVKMSCKAS<u>GYTFTS YWIT</u>WVKQRPGQGLEWIG<u>DIYPGSGSTNYNEKFKS</u>KATLTVDTSSSTAYM QLSSLTSEDSAVYYC<u>ARGGTRFSPFAY</u>WGQGTLVTVSAA.

8B12 light chain VL: Leader sequence-FR1-CDR1-FR2-CDR2-FR3-CDR3-FR4 (Leader sequence bolded. CDRs1-3 underlined):
DNA sequence (405 bp; SEQ ID NO: 20)
**ATGAAGATGCCTGTTAGGCTGTTGGTGCTGATGTTCTGGATTCCTGCTTC

CAGCAGT**GATGTTTTGATGACCCAAACTCCACTCTCCCTGCCTGTCAGTC

TTGGAGATCAAGCCTCCATCTCTTGC<u>AGATCTAGTCAGAGCATTGTACAT

AGTAATGGAAACACCTATTTAGAA</u>TGGTACCTGCAGAAACCAGGCCAGTC

TCCAAAGCTCCTGATCTAC<u>AAAGTTTCCAACCGATTTTCT</u>GGGGTCCCAG

ACAGGTTCAGTGGCAGTGGATCAGGGACAGATTTCACACTCAAGATCAGC

AGAGTGGAGGCTGAGGATCTGGGAGTTTATTACTGC<u>TTTCAAGGTTCACA

TGTTCCGTGGACG</u>TTCGGTGGAGGCACCAAGCTGGAAATCAAACGGGCTG

ATGCT;

Amino acid sequence (138 aa; SEQ ID NO: 21)
MKMPVRLLVLMFWIPASSSDVLMTQTPLSLPVSLGDQASISC<u>RSSQSIVH SNGNTYLE</u>WYLQKPGQSPKLLIY<u>KVSNRFS</u>GVPDRFSGSGSGTDFTLKIS RVEAEDLGVYYC<u>FQGSHVPWT</u>FGGGTKLEIKRADA.

The polypeptide and coding sequences of 12B4 are listed below:

12B4 heavy chain VH: Leader sequence-FR1-CDR1-FR2-CDR2-FR3-CDR3-FR4 (Leader sequence bolded. CDRs1-3 underlined):
DNA sequence (416 bp; SEQ ID NO: 22)
**ATGGGATGGAGCTGTATCATGTTCTTTTTGGTAGCAACAGCTACAGGTGT

CCACTCC**CAGGTCCAACTGCAGCAGCCTGGGGCTGAGCTGGTAAAGCCTG

GGGCTTCAGTGAAGTTGTCCTGCAAGGCTTCT<u>GGCTACACTTTCACCAGC

TACTGGATGCAC</u>TGGGTGAAGCAGAGGCCTGGACAAGGCCTTGAGTGGAT

TGGA<u>ATGATTCATCCTAATAGTGGTAGTACTAACTACAATGAGAAGTTCA

AGAGC</u>AAGGCCACACTGACTGTAGACAAATCCTCCAGCACAGCCTACATG

CAACTCAGCAGCCTGACATCTGAGGACTCTGCGGTCTATTACTGTGCAAG

A<u>TATTACTACGGTAGTAGCTATGCTATGGACTAC</u>TGGGGTCAAGGAACCT

CAGTCACCGTCTCTCA;

Amino acid sequence (138 aa; SEQ ID NO: 23)
MGWSCIMFFLVATATGVHSQVQLQQPGAELVKPGASVKLSCKAS<u>GYTFTS YWMH</u>WVKQRPGQGLEWIG<u>MIHPNSGSTNYNEKFKS</u>KATLTVDKSSSTAYM QLSSLTSEDSAVYYC<u>ARYYYGSSYAMDY</u>WGQGTSVTVS.

12B4 light chain VL: Leader sequence-FR1-CDR1-FR2-CDR2-FR3-CDR3-FR4 (Leader sequence bolded. CDRs1-3 underlined):
DNA sequence (394 bp; SEQ ID NO: 24)
**ATGGATTTTCAGGTGCAGATTTTCAGCTTCCTGCTAATCAGTGCCTCAGT

CATAATGTCCAGAGGA**CAAATTGTTCTCACCCAGTCTCCAGCAATCATGT

CTGCATCTCCAGGGGAGAAGGTCACCATAACCTGC<u>AGTGCCAGCTCAAGT

GTAAGTTACATGCAC</u>TGGTTCCAGCAGAAGCCAGGCACTTCTCCCAAACT

CTGGATTTAT<u>AGCACATCCAACCTGGCTTCT</u>GGAGTCCCTGCTCGCTTCA

GTGGCAGTGGATCTGGGACCTCTTACTCTCTCACAATCAGCCGAATGGAG

GCTGAAGATGCTGCCACTTATTACTGC<u>CAGCAAAGGAGTAGTTACCCGTA

CACGTTC</u>GGAGGGGGGACCAAGCTGGAAATAAAACGGGCTGATG;

Amino acid sequence (131 aa; SEQ ID NO: 25)
MDFQVQIFSFLLISASVIMSRGQIVLTQSPAIMSASPGEKVTITC<u>SASSS VSYMH</u>WFQQKPGTSPKLWIY<u>STSNLAS</u>GVPARFSGSGSGTSYSLTISRME AEDAATYYC<u>QQRSSYPYT</u>FGGGTKLEIKRAD.

The polypeptide and coding sequences of 24D12 are listed below:

```
24D12 heavy chain VH: Leader sequence-FR1-
CDR1-FR2-CDR2-FR3-CDR3-FR4 (Leader sequence
bolded. CDRs1-3 underlined):
DNA sequence (399 bp; SEQ ID NO: 26)
```
ATGGGATGGAGCTGTATCATGTTCTTTTTGGTAGCAACAGCTACAGGTGT

CCACTCCCAGGTCCAACTGCAGCAGCCTGGGGCTGAGCTGGTAAAGCCTG

GGGCTTCAGTGAAGTTGTCCTGCAAGGCTTCT<u>GGCTACACTTTCACCAGC

TACTGGATGCAC</u>TGGGTGAAGCAGAGGCCTGGACAAGGCCTTGAGTGGAT

TGGA<u>ATGATTCATCCTAATAGTGGTAGTACTAACTACAATGAGAAGTTCA

AGAGC</u>AAGGCCACACTGACTGTAGACAAATCCTCCAGCACAGCCTACATG

CAACTCAGCAGCCTGACATCTGAGGACTCTGCGGTCTATTACTGTGCAAA

T<u>TACTACGGTACTAATGTCTGGGG</u>CACAGGGACCACGGTCACCGTCTCT;

Amino acid sequence (133 aa; SEQ ID NO: 27)
MGWSCIMFFLVATATGVHSQVQLQQPGAELVKPGASVKLSCKAS<u>GYTFTS YWMH</u>WVKQRPGQGLEWIGM<u>IHPNSGSTNYNEKFKS</u>KATLTVDKSSSTAYM QLSSLTSEDSAVYYCAN<u>YYGTNV</u>WGTGTTVTVS.

```
24D12 light chain VL: Leader sequence-FR1-
CDR1-FR2-CDR2-FR3-CDR3-FR4 (Leader sequence
bolded. CDRs1-3 underlined):
DNA sequence (387 bp; SEQ ID NO: 28)
```
**ATGGAGACAGACACACTGCTGCTATGGGTACTGCTGCTCTGGGTTCCAGG

TTCCACTGGT**GACATTGTGCTGACACAGTCTCCTGCTTCCTTAGCTGTAT

CTCTGGGGCAGAGGGCCACCATCTCATACAGGGCCAGC<u>AAAAGTGTCAGT

ACATCTGGCTATAGTTATATGCAC</u>TGGAACCAACAGAAACCAGGACAGCC

ACCCAGACTCCTCATCTAT<u>CTTGTATCCAACC</u>TAGAATCTGGGGTCCCTG

CCAGGTTCAGTGGCAGTGGGTCTGGGACAGACTTCACCCTCAACATCCAT

CCTGTGGAGGAGGAGGATGCTGCAACCTATTACTGT<u>CAGCACATTAGGGA

AGCTTACACGTTCGGAAGGGGGG</u>ACCAAAGCTGGAAA;

Amino acid sequence (132 aa; SEQ ID NO: 29)
METDTLLLWVLLLWVPGSTGDIVLTQSPASLAVSLGQRATISYRAS<u>KSVS TSGYSYMH</u>WNQQKPGQPPRLLIY<u>LVSNLES</u>GVPARFSGSGSGTDFTLNIH PVEEEDAATYYC<u>QHIREAYT</u>FGRGDQSWK.

REFERENCES

1. Picarda, E., Ohaegbulam, K. C. & Zang, X. Molecular Pathways: Targeting B7-H3 (CD276) for Human Cancer Immunotherapy. Clin Cancer Res 22, 3425-3431 (2016).
2. Zang, X. & Allison, J. P. The B7 family and cancer therapy: costimulation and coinhibition. Clin Cancer Res 13, 5271-5279 (2007).
3. Zang, X., et al. B7-H3 and B7x are highly expressed in human prostate cancer and associated with disease spread and poor outcome. Proc Natl Acad Sci USA 104, 19458-19463 (2007).
4. Sun, T. W., et al. B7-H3 is expressed in human hepatocellular carcinoma and is associated with tumor aggressiveness and postoperative recurrence. Cancer Immunol Immunother 61, 2171-2182 (2012).
5. Wang, J., et al. B7-H3 associated with tumor progression and epigenetic regulatory activity in cutaneous melanoma. J Invest Dermatol 133, 2050-2058 (2013).
6. Hu, Y., et al. Expression of costimulatory molecule B7-H3 and its prognostic implications in human acute leukemia. Hematology 20, 187-195 (2015).
7. Sun, J., et al. B7-H3 expression in breast cancer and upregulation of VEGF through gene silence. Onco Targets Ther 7, 1979-1986 (2014).
8. Zang, X., et al. Tumor associated endothelial expression of B7-H3 predicts survival in ovarian carcinomas. Mod Pathol 23, 1104-1112 (2010).
9. Chen, Y., et al. The coexpression and clinical significance of costimulatory molecules B7-H1, B7-H3, and B7-H4 in human pancreatic cancer. Onco Targets Ther 7, 1465-1472 (2014).
10. Ingebrigtsen, V. A., et al. B7-H3 expression in colorectal cancer: associations with clinicopathological parameters and patient outcome. BMC Cancer 14, 602 (2014).
11. Sun, Y., et al. B7-H3 and B7-H4 expression in non-small-cell lung cancer. Lung Cancer 53, 143-151 (2006).
12. Xylinas, E., et al. Association of T-cell co-regulatory protein expression with clinical outcomes following radical cystectomy for urothelial carcinoma of the bladder. Eur J Surg Oncol 40, 121-127 (2014).
13. Qin, X., et al. B7-H3 is a new cancer-specific endothelial marker in clear cell renal cell carcinoma. Onco Targets Ther 6, 1667-1673 (2013).
14. Baral, A., Ye, H. X., Jiang, P. C., Yao, Y. & Mao, Y. B7-H3 and B7-H1 expression in cerebral spinal fluid and tumor tissue correlates with the malignancy grade of glioma patients. Oncol Lett 8, 1195-1201 (2014).
15. Wang, L., et al. B7-H3 is overexpressed in patients suffering osteosarcoma and associated with tumor aggressiveness and metastasis. PLoS One 8, e70689 (2013).
16. Vigdorovich, V., et al. Structure and T cell inhibition properties of B7 family member, B7-H3. Structure 21, 707-717 (2013).
17. Zhao, R., et al. HHLA2 is a member of the B7 family and inhibits human CD4 and CD8 T-cell function. Proc Natl Acad Sci USA 110, 9879-9884 (2013).

What is claimed is:

1. An antibody or an antigen-binding fragment thereof that specifically binds to an IgV domain of a B7-H3 protein; wherein the antibody is monoclonal 8B12 or the antigen-binding fragment thereof is an antigen binding fragment of the monoclonal 8B12 antibody comprising:
   (a) a VH region comprising: CDR1 consisting of the amino acid sequence set forth in SEQ ID NO: 1, CDR2 consisting of the amino acid sequence set forth in SEQ ID NO: 2, and CDR3 consisting of the amino acid sequence set forth in SEQ ID NO: 3; and
   (b) a VL region comprising: CDR1 consisting of the amino acid sequence set forth in SEQ ID NO: 4, CDR2 consisting of the amino acid sequence set forth in SEQ ID NO: 5, and CDR3 consisting of the amino acid sequence set forth in SEQ ID NO: 6; or
   wherein the antibody is monoclonal 12B4 or the antigen-binding fragment thereof is an antigen binding fragment of the monoclonal 12B4 antibody comprising:
   (a) a VH region comprising: CDR1 consisting of the amino acid sequence set forth in SEQ ID NO: 7, CDR2 consisting of the amino acid sequence set forth in SEQ ID NO: 8, and CDR3 consisting of the amino acid sequence set forth in SEQ ID NO: 9; and
   (b) a VL region comprising: CDR1 consisting of the amino acid sequence set forth in SEQ ID NO: 10, CDR2 consisting of the amino acid sequence set forth in SEQ ID NO: 11, and CDR3 consisting of the amino acid sequence set forth in SEQ ID NO: 12; or
   wherein the antibody is monoclonal 24D12 or the antigen-binding fragment thereof is an antigen binding fragment of the monoclonal 24D12 antibody comprising:
   (a) a VH region comprising: CDR1 consisting of the amino acid sequence set forth in SEQ ID NO: 7, CDR2 consisting of the amino acid sequence set forth in SEQ ID NO: 8, and CDR3 consisting of the amino acid sequence set forth in SEQ ID NO: 15; and
   (b) a VL region comprising: CDR1 consisting of the amino acid sequence set forth in SEQ ID NO: 13, CDR2 consisting of the amino acid sequence set forth in SEQ ID NO: 14, and CDR3 consisting of the amino acid sequence set forth in SEQ ID NO: 16.

2. The antibody or the antigen-binding fragment thereof of claim 1, further comprising an antigen-binding fragment of a monoclonal antibody that binds to a CD3 component of a T-cell receptor (TCR) complex on T cells.

3. The antibody or the antigen-binding fragment thereof of claim 1, further comprising a detectable marker.

4. The antibody or the antigen-binding fragment thereof of claim 1, further comprising a cytotoxic agent conjugated thereto.

5. The antigen or the antigen-binding fragment thereof of claim 1, for use in the manufacture of a medicament.

6. A composition comprising an isolated nucleic acid comprising a nucleotide sequence that encodes a CDR of the antibody or the antigen-binding fragment thereof of claim 1.

7. The composition of claim 6, further comprising a host cell or a vector comprising the isolated nucleic acid of claim 6.

8. An antibody or an antigen-binding fragment thereof that specifically binds to an IgV domain of a B7-H3 protein; wherein the antibody is humanized 8B12 or the antigen-binding fragment thereof is an antigen binding fragment of the humanized 8B12 antibody comprising:
   (a) a VH region comprising: CDR1 consisting of the amino acid sequence set forth in SEQ ID NO: 1, CDR2 consisting of the amino acid sequence set forth in SEQ ID NO: 2, and CDR3 consisting of the amino acid sequence set forth in SEQ ID NO: 3; and
   (b) a VL region comprising: CDR1 consisting of the amino acid sequence set forth in SEQ ID NO: 4, CDR2 consisting of the amino acid sequence set forth in SEQ ID NO: 5, and CDR3 consisting of the amino acid sequence set forth in SEQ ID NO: 6; or
   wherein the antibody is humanized 12B4 or the antigen-binding fragment thereof is an antigen binding fragment of the humanized 12B4 antibody comprising:
   (a) a VH region comprising: CDR1 consisting of the amino acid sequence set forth in SEQ ID NO: 7, CDR2 consisting of the amino acid sequence set forth in SEQ ID NO: 8, and CDR3 consisting of the amino acid sequence set forth in SEQ ID NO: 9; and
(b) a VL region comprising: CDR1 consisting of the amino acid sequence set forth in SEQ ID NO: 10, CDR2 consisting of the amino acid sequence set forth in SEQ ID NO: 11, and CDR3 consisting of the amino acid sequence set forth in SEQ ID NO: 12; or wherein the antibody is humanized 24D12 or the antigen-binding fragment thereof is an antigen binding fragment of the humanized 24D12 antibody comprising:
(a) a VH region comprising: CDR1 consisting of the amino acid sequence set forth in SEQ ID NO: 7, CDR2 consisting of the amino acid sequence set forth in SEQ ID NO: 8, and CDR3 consisting of the amino acid sequence set forth in SEQ ID NO: 15; and
(b) a VL region comprising: CDR1 consisting of the amino acid sequence set forth in SEQ ID NO: 13, CDR2 consisting of the amino acid sequence set forth in SEQ ID NO: 14, and CDR3 consisting of the amino acid sequence set forth in SEQ ID NO: 16.

9. The antibody or the antigen-binding fragment thereof of claim 8, further comprising a detectable marker.

10. The antibody or the antigen-binding fragment thereof of claim 8, further comprising a cytotoxic agent conjugated thereto.

11. The antigen or the antigen-binding fragment thereof of claim 8 for use in the manufacture of a medicament.

12. A composition comprising an isolated nucleic acid comprising a nucleotide sequence that encodes a CDR of the antibody or the antigen-binding fragment thereof of claim 8.

13. The composition of claim 12, further comprising a host cell or a vector comprising the isolated nucleic acid of claim 12.

* * * * *

SEQUENCE LISTING

<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: 8B12 heavy chain VH CDR1

<400> SEQUENCE: 1

```
Gly Tyr Thr Phe Thr Ser Tyr Trp Ile Thr
1               5                   10

<210> SEQ ID NO 2
<211> LENGTH: 17
<212> TYPE: PRT
<213> ORGANISM: Artificial Sequence
<220> FEATURE:
<223> OTHER INFORMATION: 8B12 heavy chain VH CDR2

<400> SEQUENCE: 2

Asp Ile Tyr Pro Gly Ser Gly Ser Thr Asn Tyr Asn Glu Lys Phe Lys
1               5                   10                  15

Ser

<210> SEQ ID NO 3
<211> LENGTH: 12
<212> TYPE: PRT
<213> ORGANISM: Artificial Sequence
<220> FEATURE:
<223> OTHER INFORMATION: 8B12 heavy chain VH CDR3

<400> SEQUENCE: 3

Ala Arg Gly Gly Thr Arg Phe Ser Pro Phe Ala Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: 8B12 light chain VL CDR1

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: 8B12 light chain VL CDR2

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 8B12 light chain VL CDR3

<400> SEQUENCE: 6

Phe Gln Gly Ser His Val Pro Trp Thr
1               5

<210> SEQ ID NO 7
<211> LENGTH: 10
<212> TYPE: PRT
<213> ORGANISM: Artificial Sequence
<220> FEATURE:
<223> OTHER INFORMATION: 12B4 & 24D12 heavy chain VH CDR1

<400> SEQUENCE: 7
```

```
Gly Tyr Thr Phe Thr Ser Tyr Trp Met His
1               5                   10
```

<210> SEQ ID NO 8
<211> LENGTH: 17
<212> TYPE: PRT
<213> ORGANISM: Artificial Sequence
<220> FEATURE:
<223> OTHER INFORMATION: 12B4 and 24D12 heavy chain VH CDR2

<400> SEQUENCE: 8

```
Met Ile His Pro Asn Ser Gly Ser Thr Asn Tyr Asn Glu Lys Phe Lys
1               5                   10                  15

Ser
```

<210> SEQ ID NO 9
<211> LENGTH: 11
<212> TYPE: PRT
<213> ORGANISM: Artificial Sequence
<220> FEATURE:
<223> OTHER INFORMATION: 12B4 heavy chain VH CDR3

<400> SEQUENCE: 9

```
Tyr Tyr Tyr Gly Ser Ser Tyr Ala Met Asp Tyr
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: 12B4 light chain VL CDR1

<400> SEQUENCE: 10

```
Ser Ala Ser Ser Ser Val Ser Tyr Met His
1               5                   10
```

<210> SEQ ID NO 11
<211> LENGTH: 7
<212> TYPE: PRT
<213> ORGANISM: Artificial Sequence
<220> FEATURE:
<223> OTHER INFORMATION: 12B4 light chain VL CDR3

<400> SEQUENCE: 11

```
Ser Thr Ser Asn Leu Ala Ser
1               5
```

<210> SEQ ID NO 12
<211> LENGTH: 9
<212> TYPE: PRT
<213> ORGANISM: Artificial Sequence
<220> FEATURE:
<223> OTHER INFORMATION: 12B4 light chain VL CDR3

<400> SEQUENCE: 12

```
Gln Gln Arg Ser Ser Tyr Pro Tyr Thr
1               5
```

<210> SEQ ID NO 13
<211> LENGTH: 12
<212> TYPE: PRT
<213> ORGANISM: Artificial Sequence
<220> FEATURE:
<223> OTHER INFORMATION: 24D12 light chain VL CDR1

-continued

```
<400> SEQUENCE: 13

Lys Ser Val Ser Thr Ser Gly Tyr Ser Tyr Met His
1               5                  10

<210> SEQ ID NO 14
<211> LENGTH: 7
<212> TYPE: PRT
<213> ORGANISM: Artificial Sequence
<220> FEATURE:
<223> OTHER INFORMATION: 24D12 light chain VL CDR2

<400> SEQUENCE: 14

Leu Val Ser Asn Leu Glu Ser
1               5

<210> SEQ ID NO 15
<211> LENGTH: 6
<212> TYPE: PRT
<213> ORGANISM: Artificial Sequence
<220> FEATURE:
<223> OTHER INFORMATION: 24D12 heavy chain VH CDR3

<400> SEQUENCE: 15

Tyr Tyr Gly Thr Asn Val
1               5

<210> SEQ ID NO 16
<211> LENGTH: 8
<212> TYPE: PRT
<213> ORGANISM: Artificial Sequence
<220> FEATURE:
<223> OTHER INFORMATION: 12D12 light chain VL CDR3

<400> SEQUENCE: 16

Gln His Ile Arg Glu Ala Tyr Thr
1               5

<210> SEQ ID NO 17
<211> LENGTH: 534
<212> TYPE: PRT
<213> ORGANISM: Homo sapiens

<400> SEQUENCE: 17

Met Leu Arg Arg Arg Gly Ser Pro Gly Met Gly Val His Val Gly Ala
1               5                  10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
        50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140
```

-continued

```
Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
            165                 170                 175

Phe Trp Gln Asp Gly Gln Gly Val Pro Leu Thr Gly Asn Val Thr Thr
        180                 185                 190

Ser Gln Met Ala Asn Glu Gln Gly Leu Phe Asp Val His Ser Ile Leu
    195                 200                 205

Arg Val Val Leu Gly Ala Asn Gly Thr Tyr Ser Cys Leu Val Arg Asn
210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
            245                 250                 255

Val Ala Leu Val Gly Thr Asp Ala Thr Leu Arg Cys Ser Phe Ser Pro
        260                 265                 270

Glu Pro Gly Phe Ser Leu Ala Gln Leu Asn Leu Ile Trp Gln Leu Thr
    275                 280                 285

Asp Thr Lys Gln Leu Val His Ser Phe Thr Glu Gly Arg Asp Gln Gly
290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
            325                 330                 335

Ser Phe Thr Cys Phe Val Ser Ile Arg Asp Phe Gly Ser Ala Ala Val
        340                 345                 350

Ser Leu Gln Val Ala Ala Pro Tyr Ser Lys Pro Ser Met Thr Leu Glu
    355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
        420                 425                 430

Asn Gly Thr Tyr Ser Cys Leu Val Arg Asn Pro Val Leu Gln Gln Asp
    435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
        500                 505                 510

Ser Lys Thr Ala Leu Gln Pro Leu Lys His Ser Asp Ser Lys Glu Asp
    515                 520                 525

Asp Gly Gln Glu Ile Ala
    530

<210> SEQ ID NO 18
<211> LENGTH: 419
<212> TYPE: DNA
```

<213> ORGANISM: Artificial Sequence
<220> FEATURE:
<223> OTHER INFORMATION: 8B12 heavy chain VH

<400> SEQUENCE: 18

```
atggaatgga gctgggtcat cctcattttg gtagcagcag ctacaggtgt ccactcccag    60
gtccaactgc agcagcctgg ggctgagctt gtgaagcctg ggcttcagt gaagatgtcc    120
tgcaaggctt ctggctacac cttcaccagc tactggataa cctgggtgaa gcagaggcct    180
ggacaaggcc ttgagtggat tggagatatt tatcctggta gtggtagtac taactacaat    240
gagaagttca gagcaaggc cactctgact gtagacacat cctccagcac agcctacatg    300
cagctcagca gcctgacatc tgaggactct gcggtctatt actgtgcaag gggggtact   360
agattcagcc cctttgctta ctggggccaa gggactctgg tcactgtctc tgcagctac    419
```

<210> SEQ ID NO 19
<211> LENGTH: 139
<212> TYPE: PRT
<213> ORGANISM: Artificial Sequence
<220> FEATURE:
<223> OTHER INFORMATION: 8B12 heavy chain VH

<400> SEQUENCE: 19

```
Met Glu Trp Ser Trp Val Ile Leu Ile Leu Val Ala Ala Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Trp Ile Thr Trp Val Lys Gln Arg Pro Gly Gln Gly Leu
    50                  55                  60

Glu Trp Ile Gly Asp Ile Tyr Pro Gly Ser Gly Ser Thr Asn Tyr Asn
65                  70                  75                  80

Glu Lys Phe Lys Ser Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Gly Thr Arg Phe Ser Pro Phe Ala Tyr Trp
        115                 120                 125

Gly Gln Gly Thr Leu Val Thr Val Ser Ala Ala
    130                 135
```

<210> SEQ ID NO 20
<211> LENGTH: 405
<212> TYPE: DNA
<213> ORGANISM: Artificial Sequence
<220> FEATURE:
<223> OTHER INFORMATION: 8B12 light chain VL

<400> SEQUENCE: 20

```
atgaagatgc tgttaggct gttggtgctg atgttctgga ttcctgcttc cagcagtgat    60
gttttgatga cccaaactcc actctccctg cctgtcagtc ttggagatca agcctccatc    120
tcttgcagat ctagtcagag cattgtacat agtaatggaa acacctattt gaatggtac    180
ctgcagaaac aggccagtc tccaaagctc ctgatctaca agtttccaa ccgattttct    240
ggggtcccag acaggttcag tggcagtgga tcagggacag atttcacact caagatcagc    300
agagtggagg ctgaggatct gggagtttat tactgctttc aaggttcaca tgttccgtgg    360
```

```
acgttcggtg gaggcaccaa gctggaaatc aaacgggctg atgct           405
```

```
<210> SEQ ID NO 21
<211> LENGTH: 135
<212> TYPE: PRT
<213> ORGANISM: Artificial Sequence
<220> FEATURE:
<223> OTHER INFORMATION: 8B12 light chain VL

<400> SEQUENCE: 21
```

```
Met Lys Met Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys Arg Ala Asp Ala
    130                 135
```

```
<210> SEQ ID NO 22
<211> LENGTH: 416
<212> TYPE: DNA
<213> ORGANISM: Artificial Sequence
<220> FEATURE:
<223> OTHER INFORMATION: 12B4 heavy chain VH

<400> SEQUENCE: 22
atgggatgga gctgtatcat gttcttttg gtagcaacag ctacaggtgt ccactcccag    60
gtccaactgc agcagcctgg ggctgagctg gtaaagcctg gggcttcagt gaagttgtcc  120
tgcaaggctt ctggctacac tttcaccagc tactggatgc actgggtgaa gcagaggcct  180
ggacaaggcc ttgagtggat tggaatgatt catcctaata gtggtagtac taactacaat  240
gagaagttca agagcaaggc cacactgact gtagacaaat cctccagcac agcctacatg  300
caactcagca gcctgacatc tgaggactct gcggtctatt actgtgcaag atattactac  360
ggtagtagct atgctatgga ctactggggt caaggaacct cagtcaccgt ctctca      416
```

```
<210> SEQ ID NO 23
<211> LENGTH: 138
<212> TYPE: PRT
<213> ORGANISM: Artificial Sequence
<220> FEATURE:
<223> OTHER INFORMATION: 12B4 heavy chain VH

<400> SEQUENCE: 23
```

```
Met Gly Trp Ser Cys Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30
```

```
Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
 50                  55                  60

Glu Trp Ile Gly Met Ile His Pro Asn Ser Gly Ser Thr Asn Tyr Asn
 65                  70                  75                  80

Glu Lys Phe Lys Ser Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Tyr Gly Ser Ser Tyr Ala Met Asp Tyr
            115                 120                 125

Trp Gly Gln Gly Thr Ser Val Thr Val Ser
    130                 135
```

<210> SEQ ID NO 24
<211> LENGTH: 394
<212> TYPE: DNA
<213> ORGANISM: Artificial Sequence
<220> FEATURE:
<223> OTHER INFORMATION: 12B4 light chain VL

<400> SEQUENCE: 24

```
atggatttc aggtgcagat tttcagcttc ctgctaatca gtgcctcagt cataatgtcc      60
agaggacaaa ttgttctcac ccagtctcca gcaatcatgt ctgcatctcc aggggagaag    120
gtcaccataa cctgcagtgc cagctcaagt gtaagttaca tgcactggtt ccagcagaag    180
ccaggcactt ctcccaaact ctggatttat agcacatcca acctggcttc tggagtccct    240
gctcgcttca gtggcagtgg atctgggacc tcttactctc tcacaatcag ccgaatggag    300
gctgaagatg ctgccactta ttactgccag caaaggagta gttacccgta cacgttcgga    360
ggggggacca agctggaaat aaaacgggct gatg                                 394
```

<210> SEQ ID NO 25
<211> LENGTH: 131
<212> TYPE: PRT
<213> ORGANISM: Artificial Sequence
<220> FEATURE:
<223> OTHER INFORMATION: 12B4 light chain VL

<400> SEQUENCE: 25

```
Met Asp Phe Gln Val Gln Ile Phe Ser Phe Leu Leu Ile Ser Ala Ser
 1               5                  10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
            35                  40                  45

Ser Ser Val Ser Tyr Met His Trp Phe Gln Gln Lys Pro Gly Thr Ser
 50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Met Glu Ala Glu Asp Ala Ala Thr Tyr Tyr Cys Gln Gln Arg
            100                 105                 110

Ser Ser Tyr Pro Tyr Thr Phe Gly Gly Gly Thr Lys Leu Glu Ile Lys
            115                 120                 125
```

Arg Ala Asp
    130

<210> SEQ ID NO 26

<400> SEQUENCE: 26

000

<210> SEQ ID NO 27
<211> LENGTH: 133
<212> TYPE: PRT
<213> ORGANISM: Artificial Sequence
<220> FEATURE:
<223> OTHER INFORMATION: 24D12 heavy chain VH

<400> SEQUENCE: 27

Met Gly Trp Ser Cys Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Asn Tyr Tyr Gly Thr Asn Val Trp Gly Thr Gly Thr
        115                 120                 125

Thr Val Thr Val Ser
    130

<210> SEQ ID NO 28
<211> LENGTH: 387
<212> TYPE: DNA
<213> ORGANISM: Artificial Sequence
<220> FEATURE:
<223> OTHER INFORMATION: 24D12 light chain VL

<400> SEQUENCE: 28
atggagacag acacactgct gctatgggta ctgctgctct gggttccagg ttccactggt      60
gacattgtgc tgacacagtc tcctgcttcc ttagctgtat ctctggggca gagggccacc     120
atctcataca gggccagcaa aagtgtcagt acatctggct atagttatat gcactggaac     180
caacagaaac caggacagcc acccagactc ctcatctatc ttgtatccaa cctagaatct     240
ggggtccctg ccaggttcag tggcagtggg tctgggacag acttcaccct caacatccat     300
cctgtggagg aggaggatgc tgcaacctat tactgtcagc acattaggga agcttacacg     360
ttcggaaggg gggaccaaag ctggaaa                                         387

<210> SEQ ID NO 29
<211> LENGTH: 129
<212> TYPE: PRT
<213> ORGANISM: Artificial Sequence
<220> FEATURE:
<223> OTHER INFORMATION: 24D12 light chain VL

```
<400> SEQUENCE: 29

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Tyr Arg Ala Ser Lys Ser
            35                  40                  45

Val Ser Thr Ser Gly Tyr Ser Tyr Met His Trp Asn Gln Gln Lys Pro
        50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
                100                 105                 110

Gln His Ile Arg Glu Ala Tyr Thr Phe Gly Arg Gly Asp Gln Ser Trp
            115                 120                 125

Lys
```